United States Patent
Nagesh Subramanya et al.

(10) Patent No.: US 10,541,055 B2
(45) Date of Patent: Jan. 21, 2020

(54) VISUAL ALARM INDICATION ON PARAMETER ACTIVE CABLES

(71) Applicant: General Electric Company, Schenectady, NY (US)

(72) Inventors: Kartheek Nagesh Subramanya, Bangalore (IN); Ganesan Kaliamoorthy, Bangalore (IN)

(*) Notice: Subject to any disclaimer, the term of this patent is extended or adjusted under 35 U.S.C. 154(b) by 89 days.

(21) Appl. No.: 15/536,441

(22) PCT Filed: Jul. 1, 2015

(86) PCT No.: PCT/US2015/038800
§ 371 (c)(1),
(2) Date: Jun. 15, 2017

(87) PCT Pub. No.: WO2016/105600
PCT Pub. Date: Jun. 30, 2016

(65) Prior Publication Data
US 2017/0347970 A1    Dec. 7, 2017

(30) Foreign Application Priority Data

Dec. 23, 2014 (IN) .......................... 6495/CHE/2014

(51) Int. Cl.
*G16H 50/00* (2018.01)
*G16H 50/20* (2018.01)
*A61B 5/00* (2006.01)
*A61B 5/145* (2006.01)
*G08B 5/36* (2006.01)

(52) U.S. Cl.
CPC ........... *G16H 50/20* (2018.01); *A61B 5/0015* (2013.01); *A61B 5/14542* (2013.01); *A61B 5/746* (2013.01); *G08B 5/36* (2013.01)

(58) Field of Classification Search
CPC .. G16H 50/20; A61B 5/0015; A61B 5/14542; A61B 5/7282; A61B 5/746; A61B 2505/05; A61B 2562/06; G08B 5/36; G09G 5/006; G09G 2330/12; G06F 19/00
USPC .......................................................... 600/300
See application file for complete search history.

(56) References Cited

U.S. PATENT DOCUMENTS 5,505,199 A * 4/1996 Kim .......................... A61B 5/11
                                                          348/143
5,920,263 A * 7/1999 Huttenhoff ......... A61B 5/02455
                                                          340/573.1

(Continued)

OTHER PUBLICATIONS

International Search Report and Written Opinion for International Application No. PCT/US2015/038800, dated Oct. 6, 2015, 9 pages.

*Primary Examiner* — Carl H Layno
*Assistant Examiner* — Michael J Lau
(74) *Attorney, Agent, or Firm* — Andrus Intellectual Property Law, LLP (57) ABSTRACT

A patient monitoring system and method for visual alarm indication on parameter active cables are provided herein. The patient monitoring system includes a plurality of sensors and an active cable coupled to the plurality of sensors to acquire data from the plurality of sensors. The patient monitoring system also includes a host patient monitor coupled to the active cable, wherein the active cable includes a visual alarm that is to indicate an alarm condition using the plurality of sensors.

17 Claims, 5 Drawing Sheets

(56) References Cited

U.S. PATENT DOCUMENTS

| | | | |
|---|---|---|---|
| 8,382,666 B1* | 2/2013 | Mao | A61B 1/00121 |
| | | | 600/202 |
| 2006/0248398 A1* | 11/2006 | Neel | G16H 40/63 |
| | | | 714/33 |
| 2008/0058773 A1* | 3/2008 | John | G16H 50/20 |
| | | | 604/891.1 |
| 2011/0152628 A1* | 6/2011 | Balji | A61B 5/0002 |
| | | | 600/300 |
| 2012/0003933 A1* | 1/2012 | Baker | H04W 4/029 |
| | | | 455/41.2 |
| 2012/0179006 A1* | 7/2012 | Jansen | A61B 5/0537 |
| | | | 600/301 |
| 2013/0297330 A1* | 11/2013 | Kamen | G06F 19/3462 |
| | | | 705/2 |
| 2014/0276143 A1* | 9/2014 | Corl | A61B 5/0215 |
| | | | 600/486 |

* cited by examiner

VISUAL ALARM INDICATION ON PARAMETER ACTIVE CABLES

CROSS-REFERENCE TO RELATED APPLICATIONS

This is a national stage application under 35 U.S.C. § 371 (c) of PCT Patent Application No. PCT/US2015/038800, filed on Jul. 1, 2015, which claims priority to India Patent Application No. 6495/CHE/2014, filed on Dec. 23, 2014, the disclosures of which are incorporated herein by reference in their entireties.

BACKGROUND OF THE INVENTION

Parameter acquisition cables are used in various systems that monitor the health and condition of a patient. Typically, the cable is coupled with a plurality of sensors and a device. The plurality of sensors is attached to a patient and used to collect data from the patient. The data is transferred from the sensors to the device via the cable, where the data is analyzed and sometimes displayed by the device. The device may be a configurable or non-configurable acquisition device, an analytical device or machine, an operator workstation, user interface or display device, and the like. The data captured by the cable may be used to measure physiological data such as pulse oximetery ($SpO_2$), cardiac output (CO), temperature, blood glucose, invasive blood pressure (IBP), non-invasive blood pressure (NBP), mainstream end tidal carbon dioxide ($ETCO_2$), electrocardiography/respiration (ECG/Resp), electroencephalography (EEG), venous oxygen saturation ($SvO_2$), impedance cardiography (ICG), Bispectral Index (BIS), neuromuscular transmission (NMT), entropy monitoring, spirometry/respiratory mechanics, metabolic monitoring, anesthetic agent (i.e., gas) monitoring, and the like.

Current cables do not process data obtained from sensors attached to a patient. Further, current cables do not communicate information to a clinician. Thus, current cables miss an opportunity to provide added features to a patient monitoring system. Moreover, the placement of current cables may be limited due to potential degradation of signal transfer with no alert or indication from the cable itself.

SUMMARY OF THE INVENTION

An embodiment relates to a patient monitoring system. The patient monitoring system includes a plurality of sensors and an active cable coupled to the plurality of sensors to acquire data from the plurality of sensors. The patient monitoring system also includes a host patient monitor coupled to the active cable, wherein the active cable includes a visual alarm that is to indicate an alarm condition using the plurality of sensors.

Another embodiment relates to a method for a visual alarm indication on parameter active cables. The method includes acquiring, at the active cable, sensor data from a plurality of sensors. The data is processed at the active cable. The method also includes sending the data to a host patient monitor, indicating, on the active cable, and alarm condition from the plurality of sensors.

Still another embodiment relates to a parameter active cable. The parameter active cable includes a plurality of integrated electronics and a visible alarm indicator. The parameter active cable also includes a communication interface.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As discussed above, current cables do not provide any visual indication regarding the status of a parameter obtained by the cable. In the embodiments discussed herein, a visual alarm indication is provided on parameter active cables. Active cables as described herein may also be called or known as smart cables, intelligent cables or parameter micro modules. A technical effect of at least one embodiment includes a mechanism for analyzing data obtained from sensors using the active cable. In some scenarios, the analog signals read from acquisition sensors are converted to digital data, processed fully at the cable, and sent as parameters and waveforms to a host monitor over a communication interface. In particular, the digital data may be sent as numeric parameter and waveform values to a patient monitor over a communication interface.

In some cases, a parameter cable where analog signals are converted into digital data and sent over a communication interface to host monitor is known as a smart cable or an active cable. Parameter Active cables contain one or more microcontrollers and associated circuitry within the cable it to acquire data from sensors and process it before transferring it to the host monitor. Additionally, the parameter active cable can include a visual indication capability embedded in the cable that is to indicate an alarm condition that exists on the parameter measured by the cable. As used herein, an alarm condition is any condition that causes parameter values to be outside of a pre-determined acceptable range.

Figure 1A:
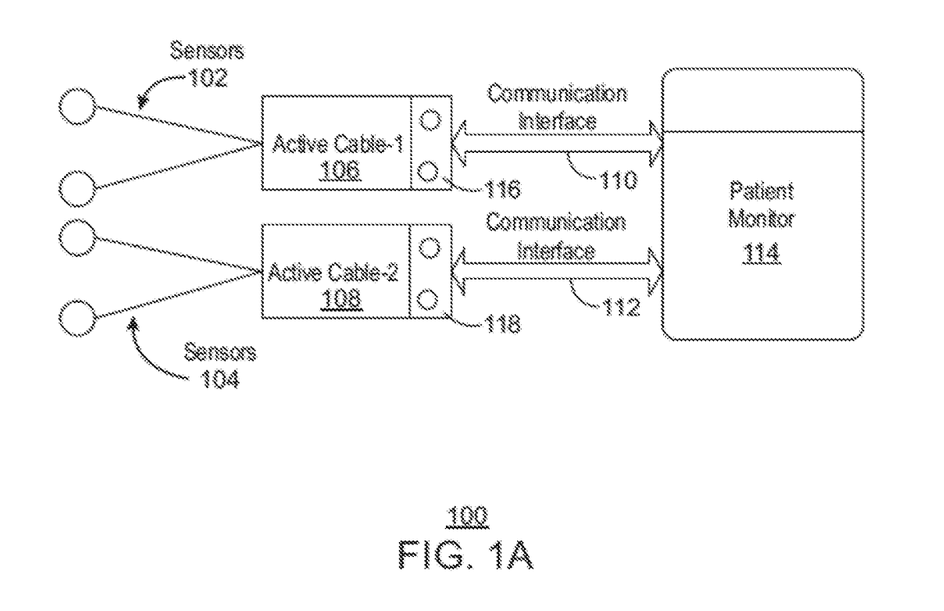
FIG. 1A is a patient monitoring system with no alarms in accordance with an embodiment.

In FIG. 1A, a patient monitoring system 100 with no alarms is depicted in accordance with an embodiment. The patient monitoring system 100 includes a plurality of sensors 102 coupled with an active cable 106. The patient monitoring system 100 also includes a plurality of sensors 104 coupled with an active cable 108. The active cable 106 is coupled with a communication interface 110, while the active cable 108 is coupled with a communication interface 112. The communication interface 110 and the communication interface 112 are used to establish a communication link with a patient monitor 114. In some cases, communication interface is adapted to connect the patient monitor 114 to a communication network to transmit data acquired by the patient monitor 114 using the plurality of sensors 102 or the plurality of sensors 104 over a communication network.

The patient monitor 114 is to monitor the patient to by obtaining physiological data such as pulse oximetry data, cardiac output data, temperature data, blood glucose data, blood pressure data, mainstream end tidal carbon dioxide data, electrocardiogram data, respiration data, electroencephalogram data, venous oxygen saturation data, impedance cardiogram data, Bispectral Index data, neuromuscular transmission data, entropy data, spirometry/respiratory mechanics data, metabolic data, anesthetic agent data, and the like. This parameter data may be presented to a clinician using a local display within the patient monitor 114. In some embodiments, the parameter data may be presented to a clinician using a remote display. Although one patient monitor is illustrated, several patient monitors may be present within the patient monitoring system 100.

In FIG. 1A, the active cable 106 and the active cable 108 each contain one or more microcontrollers and associated circuitry within the active cable to acquire data from their respective plurality of sensors, and then process the data before transferring the data to the patient monitor. In this manner, various features based on the processed data can be added to the cable. In embodiments, a form of visual indication capability is included within the active cables to indicate an alarm condition that exists on the parameter measured by the cable. As illustrated, the active cable 106 and the active cable 108 each include a plurality of visual alarms. Specifically, the active cable 106 includes visual alarm indicators 116, and the active able 108 includes visual alarm indicators 118. The visual alarm indicators 116 and the visual alarm indicators 118 can be a light emitting diode (LED) that is on when an alarm condition exists. The visual alarm indicators of the active cables can be any indicator capable of a visual change in response to an alarming condition, such as an LED, laser, field-induced polymer electroluminescent (FIPEL), and the like.

Figure 1B:
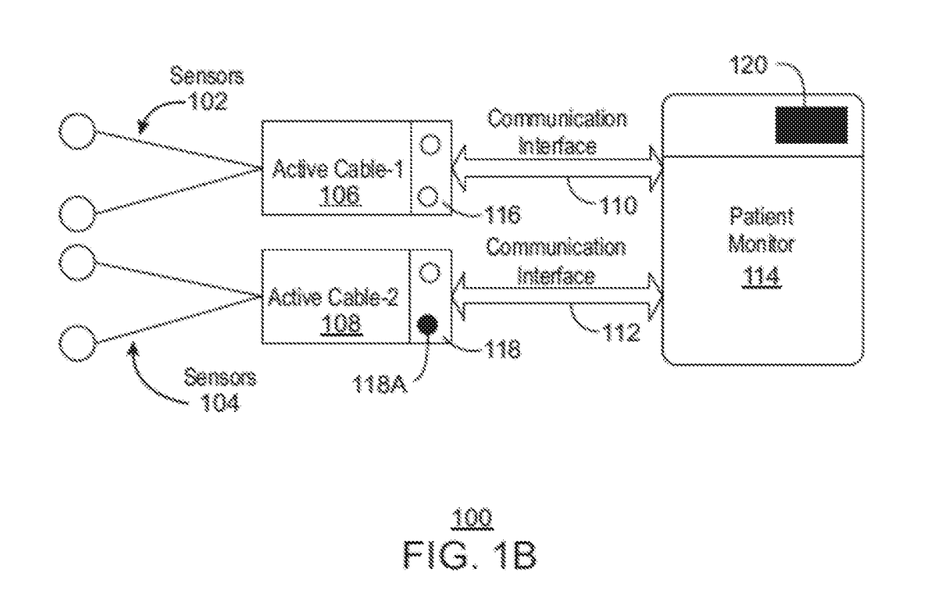
FIG. 1B is the patient monitoring system with an alarm in accordance with an embodiment.

FIG. 1B is the patient monitoring system 100 with an alarm in accordance with an embodiment. As illustrated in FIG. 1B, an alert 120 is indicated on the patient monitor 114. In embodiments, the patient monitor 114 is configured to indicate the patient status visually or audibly to a clinician by producing an alert in response to an alarm condition. A visual alarm 118A is also visually present on the active cable 108. Different forms of indication could be used to indicate the patient status based on the clinical nature of the patient, criticality of patient, and so on.

The visual alarm 118A can be used with all types of alarms, such as low, medium, and high priority alarms. The visual alarm 118A may also be selectively applied only to a high priority alarm. The visual alarm 118A indication on the active cable 108 is not intrusive enough to disturb the patient. In embodiments, the visual alarm can be disabled if the visual alarm is unnecessary under the current conditions. For example, consider a $SpO_2$ cable where the $SpO_2$ value obtained from the sensors attached to the patient are out of a normal range in that the $SpO_2$ value is either too low or too high. In a first case, an algorithm running on host patient monitor detects this condition according to preset thresholds and shows a clinical alarm on the monitor display. The host patient monitor can also plays an audio tone as audible cue to the caregiver that the $SpO_2$ values are out of a normal range. In addition to the alarm on the host patient monitor, a visual alarm is also triggered on the $SpO_2$ active cable. In embodiments, the host patient monitor can send a protocol packet over the communication interface to the $SpO_2$ active cable to trigger the visual alarm on the cable. Once the Spot level comes within normal range, a protocol packet can be sent from the host patient monitor to the active cable to turn off the visual alarm indication.

In a second use case, an algorithm running on the parameter active cable can detect an alarm condition according to preset thresholds, and cause a clinical alarm to be displayed on the host patient monitor. The cable may also cause an audio tone to play at the host patient monitor as an audible cue to the caregiver that the $SpO_2$ values are out of a normal range. A visual alarm is also triggered on the $SpO_2$ active cable, without the use of the host patient monitor, as detection of the alarm condition is embedded within the cable. Once the $SpO_2$ level comes within normal range, the cable can be used to detect the normal $SpO_2$ and turn off the visual alarm indication within the active cable without the use of the host patient monitor. The cable can also cause removal of any alert present at the host patient monitor when the alarm condition ceases to exist.

The block diagram of FIGS. 1A and 1B are not intended to indicate that the patient monitoring system 100 is to include all of the components shown in FIGS. 1A and 1B in every case. Moreover, any number of additional or alternative components not shown in FIGS. 1A and 1B may be included in the patient monitoring system 100, depending on the details of the specific implementation.

Figure 2:
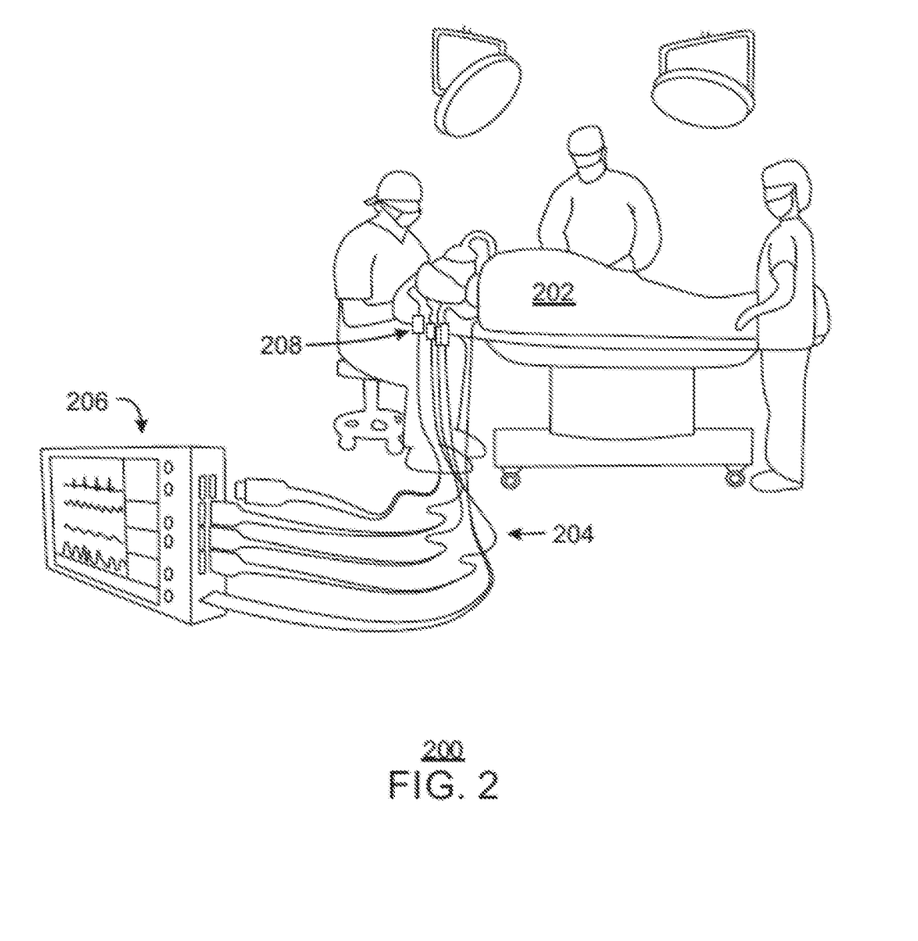
FIG. 2 is an illustration of patient monitoring system in a clinical setting.

FIG. 2 is an illustration of patient monitoring system in a clinical setting 200. The clinical setting 200 includes a patient 202 that is monitored using a plurality of sensors. The plurality of sensors are attached to a plurality of active cables 204, with are attached to a host patient monitor 206. Each of the active cables 204 includes a visual alarm indicator 208.

As illustrated, the active cables 204 are connected to the host patient monitor 206 using a universal serial bus (USB) protocol. However, the active cables can be connected to patient monitor using any standard bidirectional communication interface, such as USB, universal asynchronous receiver/transmitter (UART), peripheral component interconnect express (PCI-e), and the like. The active cables may also be an active cable according to other standards such as, Thunderbolt, Firewire, DisplayPort, and High-Definition Multimedia Interface (HDMI). In embodiments, the bidirectional communication interface enables the parameter active cables to be configured and controlled by the host patient monitor while still enabling the host patient monitor to receive parameter data. In examples, configuration includes calibration of the parameter active cables. Configuration of the cables may also include updating algorithms used by the cables to calculate parameter values and waveforms from the plurality of sensors. The host patient monitor may also control the active cables by limiting the amount of processing performed by the active cable.

The visual alarm indicators 208 can be positioned at any location along the length of the active cables 204. The visual alarm feature can be selectively enabled or disabled depending on the care area, stability of the patient, and placement of the host patient monitor and active cables. In some examples, the visual alarms are suitable to operating room scenarios or situations where the active cable visual alarm indicator does not distract the patient. The alarm functionality can be implemented through in various manners. For example, if a critical alarm condition is detected on a parameter, the host patient monitor can send a message to the active cable to turn ON the alarm indicator on the active cable. When the alarm condition ceases, another message may be sent to from the host patient monitor to turn OFF the alarm indicator on the active cable.

In embodiments, the alarm condition can also be triggered by a probes off or leads off condition on the active cable. A probe or leads off condition may occur when a sensor of the plurality of sensors is misplaced or not secured to the patient. The probe off decisions can be made either locally within the cable or assisted by host monitor.

Accordingly, the active cables have the capability to visually indicate alarming conditions. Although the visual alarm indicator 208 is illustrated near the patient 202, the active cable placements can vary according to the clinical settings and needs of the patient and caregivers. The active cables provide firsthand information visually and immediately on the parameter cable itself, which is easily understandable and can guide the caregiver to look to the host patient monitor user interface for more detailed information. This added indicator within the cable is useful in the scenario when an audio alarm from the patient monitor fails to draw attention of caregivers during high risk surgical procedures. In some cases, the audio alarm from the patient monitor can fail to draw attention, as it may be intentionally disabled.

Figure 3:
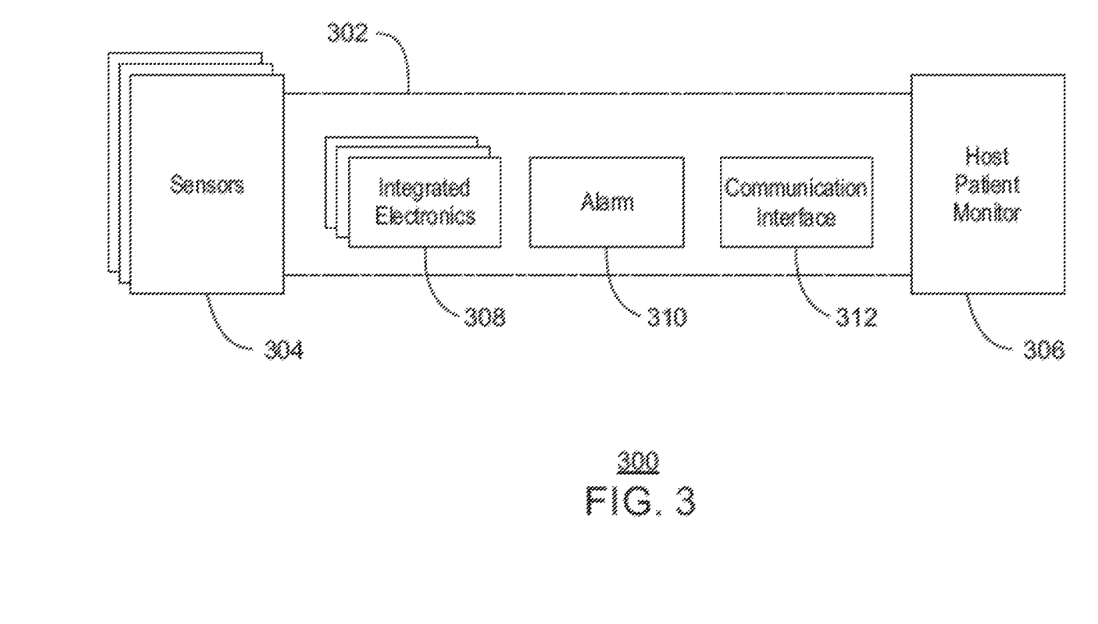
FIG. 3 is a block diagram of a patient monitoring system 300 with a parameter active cable.

FIG. 3 is a block diagram of a patient monitoring system 300 with a parameter active cable 302. The patient monitoring system 300 and the parameter active cable 302 may be similar to those described in FIGS. 1 and 2. The parameter active cable 302 may be connected to a plurality of sensors 304 and a host patient monitor 306. The parameter active cable 302 includes integrated electronic components 308, an alarm component 310, and a communications interface 312.

The integrated electronic components 308 may be powered by the host patient monitor via an internal power line connected to the host patient monitor. In some embodiments, the integrated electronic components may receive power from a standalone power source. Depending on the specific configuration of the parameter active cable 302, the integrated electronic components 308 may include a signal acquisition functionality, microcontrollers, filters, algorithms to process the signals or data acquired from the sensors, and the like. The alarm components 310 may also be powered by an internal power line and can power ON and OFF a visual alarm of the cable according to the presence of alarm conditions.

The functionality of the parameter active cable 302 may change depending on the components present in the parameter active cable 300. For example, a fully smart parameter active cable may include integrated electronic components 308 such as a signal acquisition, micro-processing, filtering, storage and the like. In an embodiment, a smart parameter active cable can convert analog data received from sensors 304 to digital data. The digital data can then be processed using algorithms stored on the cable. In some cases, a numeric parameter and waveform data results from processing the digital data. The parameter and waveform can then be sent to the host patient monitor 306 via the communications interface 312. The host patient monitor 306 then displays the parameter and waveform without any further processing. In this case, all data processing is done at the parameter active cable, with no processing at the host patient monitor. Moreover, the alarm 310 can be turned ON and OFF without any further communication from the host patient monitor, as the cable includes enough processing power to determine if an alarm condition is present. In another embodiment, parameter and waveform are sent to host patient monitor which then detects alarm condition based on threshold values preset by clinician. Host patient monitor can send protocol packets over communication interface to turn ON and OFF alarm 310. In other embodiments, the parameter active cable 302 includes integrated electronic components 308 to convert the acquired sensor data from analog to digital. The digital data may then be filtered and sent to the host patient monitor without any further processing.

The integrated electronic components 308 may also include drivers to preserve the integrity of the data signals acquired from the sensors 304. These drivers may be used, for example, to reshape and retime the data signal. In some cases, the parameter active cable 302 may be long enough such that the data signals acquired from the sensors 304 may become degraded, and may therefore lose integrity. In embodiments, the integrated electronic components 308 may perform operations on the data signals acquired from the sensors 304. The operations may include any combination of buffering, reshaping, retiming, and the like.

By implementing a portion of the data processing within the parameter active cable, the parameter active cables can be added to the host patient monitor in a "plug-and-play" fashion. In particular, the patient monitoring system can discover the addition of a cable in the patient monitoring system without a user manually configuring the cable. Further, the cable can be discovered without intervention by the user. The patient monitoring system can automatically configure the cable and can assign resources to the cable as needed. Further, the cable will automatically communicate with the host patient monitor as soon as it is attached.

The present techniques may also extend to parameter cables with limited capability to indicate alarms through some form of communication with the host. For example, in an existing parameter cable there may be no intelligence built in to the cable. The existing parameter cable may be merely a cable that provides data to the host patient monitor, without any processing. An additional intelligent portion can be added to the existing parameter cable. The additional intelligent portion can be a parameter active cable as described herein. The additional length can have a visual alarm indicator according to techniques described herein. In this manner, additional processing capability can be added to any existing parameter cable.

Figure 4:
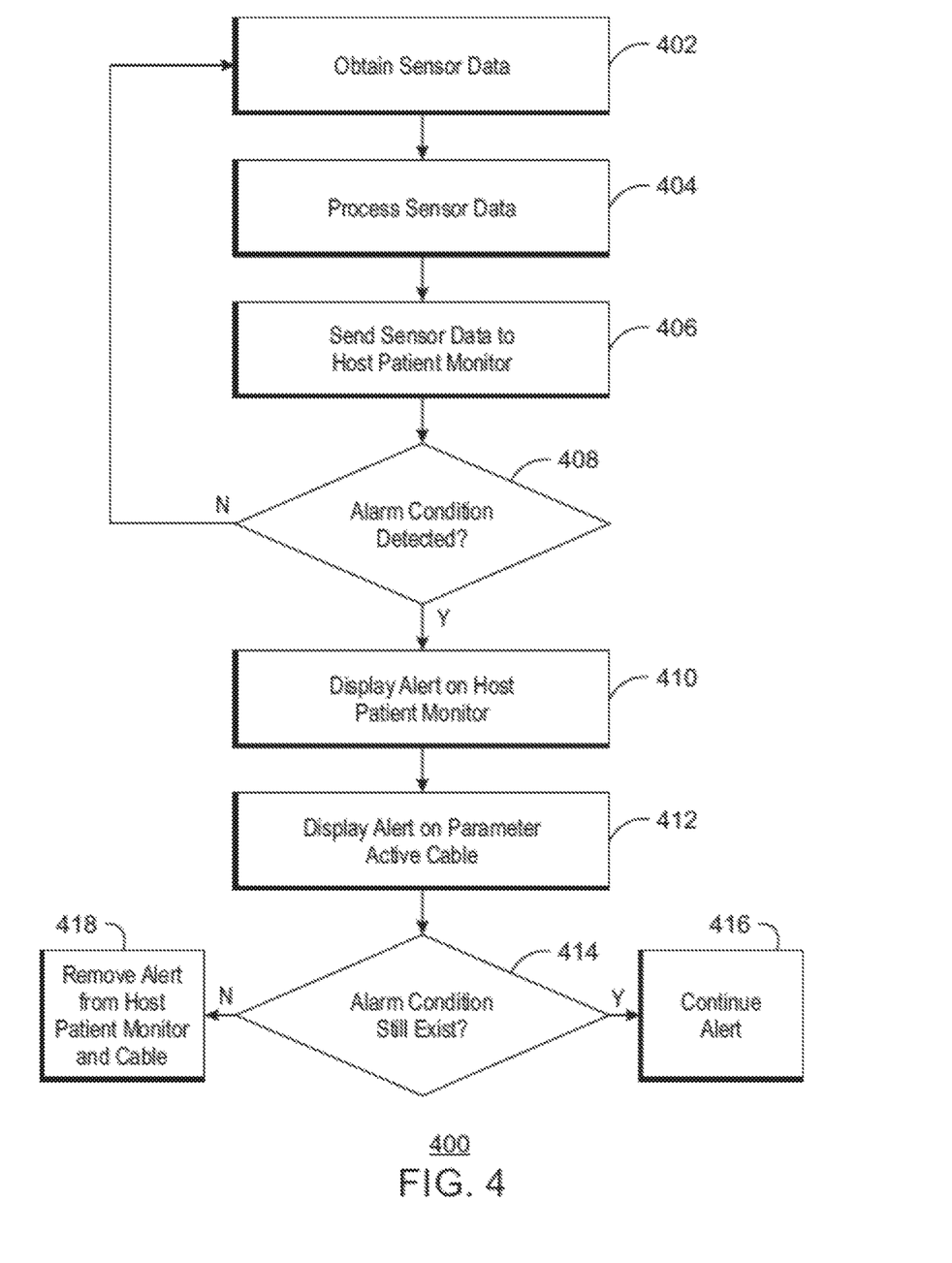
FIG. 4 is a process flow diagram of a method for visually indicating an alarm on parameter active cables as determined by the host patient monitor.

FIG. 4 is a process flow diagram of a method 500 for visually indicating an alarm on parameter active cables as determined by the host patient monitor. At block 402, a sensor data is obtained. At block 404, the data acquired from the sensors is processed. In embodiments, processing the data includes converting the data from analog to digital. Also, in embodiments, processing the data includes converting the data from analog to digital, applying algorithms to the data, and sending the resulting parameter and waveform to a host patient monitor. At block 406, the processed data is sent to the host patient monitor. If necessary, the host patient monitor then further processes the data. The data can also be displayed.

At block 408, it is determined if an alarm condition has been detected at the host. If an alarm condition has been detected at the host, process flow continues to block 410. If no alarm condition has been detected at the host, process flow returns to block 402. At block 410, if an alarm condition has been detected, the host patient monitor shows a clinical alarm on the host monitor display. The host patient monitor can also play an audio tone as audible cue to the existing alarm condition. At block 412, in addition to the alarm on the host patient monitor, a visual alarm is also triggered on the parameter active cable. In embodiments, the host patient monitor can send a protocol packet over the communication interface to the parameter active cable to trigger the visual alarm on the active cable.

At block 414, it is determined if the alarm condition still exists. If the alarm condition still exists, process flow continues to block 416. If the alarm condition does not exist, process flow continues to block 418. At block 416, the alarm continues. At block 418, the alert is removed from the host patient monitor and the parameter active cable. In embodiments, a protocol packet can be sent from the host patient monitor to the active cable to turn off the visual alarm indication.

The process flow diagram of FIG. 4 is not intended to indicate that the blocks of the method 400 are to be executed in any particular order, or that all of the blocks shown in FIG. 4 are to be included in every case. Furthermore, the method 400 may include any number of additional or alternative blocks not shown in FIG. 4, depending on the details of the specific implementation.

Figure 5:
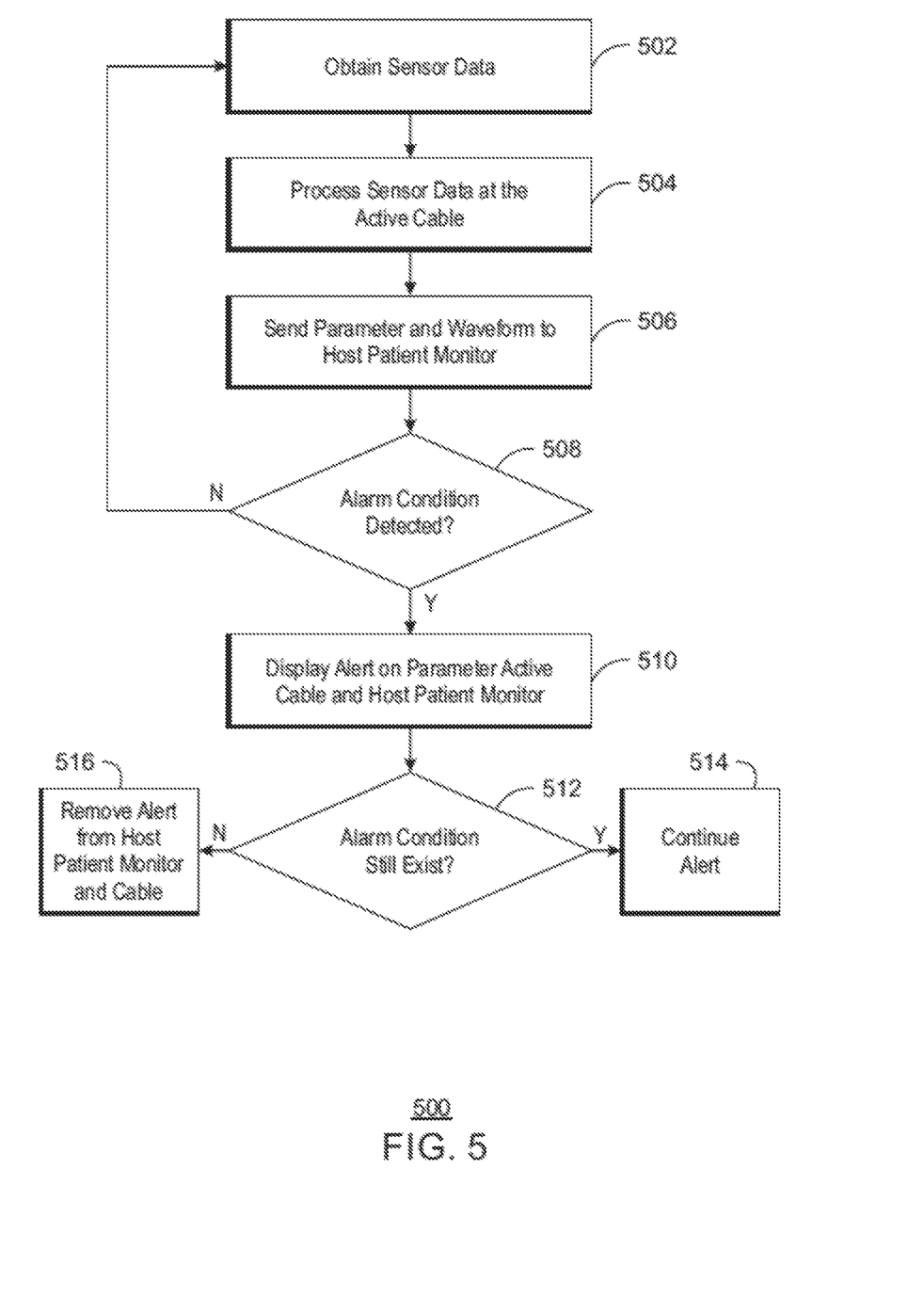
FIG. 5 is a process flow diagram of a method for visually indicating an alarm on parameter active cables as determined by the parameter active cable.

FIG. 5 is a process flow diagram of a method 500 for visually indicating an alarm on parameter active cables as determined by the parameter active cable. At block 502, a sensor data is obtained. At block 504, the data acquired from the sensors is processed by converting the data from analog to digital. Algorithms are applied to the data to obtain a parameter value and a waveform. At block 506, the parameter value and waveform are sent to the host patient monitor and can be displayed.

At block 508, it is determined if an alarm condition has been detected by the cable. If an alarm condition has been detected by the cable, process flow continues to block 510. If no alarm condition has been detected by the cable, process flow returns to block 504. At block 510, if an alarm condition has been detected by the cable, a visual alarm is also triggered on the parameter active cable. The parameter active cable can also cause an alert to display on the host patient monitor. At block 512, it is determined if the alarm condition still exists. If the alarm condition still exists, process flow continues to block 514. If the alarm condition does not exist, process flow continues to block 516. At block 514, the alarm continues. At block 516, the visual alarm indication is turned OFF at the cable. The alert can also be removed from the host patient monitor, if present.

The process flow diagram of FIG. 5 is not intended to indicate that the blocks of the method 500 are to be executed in any particular order, or that all of the blocks shown in FIG. 5 are to be included in every case. Furthermore, the method 500 may include any number of additional or alternative blocks not shown in FIG. 5, depending on the details of the specific implementation.

Adding a visual alarm indication to a parameter cable enables the parameter cables to be kept close to the patient while the bedside monitor is away from patient. Since caregiver is notified of critical alarming condition on the cable itself visually, the patient does not need to be disturbed by the alert that occurs on the bedside monitor. Further, the visual alarm indication on the cable may be used as secondary alarm from a risk assessment perspective. Also, even less skilled caregivers with less clinical knowledge can identify alarming condition from the cables and bring the condition to the attention of skilled caregivers.

While embodiments are described herein with respect to cables used in the medical field, the reference to patient monitoring systems may be interpreted broadly. Embodiments described herein can encompass those situations in which any system is used to data from a subject. Further, those of skill in the art will recognize that the present techniques are applicable to many different hardware configurations, software architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A patient monitoring system, comprising:
   a plurality of sensors;
   an active cable coupled to the plurality of sensors to acquire physiological data from the plurality of sensors; and
   a host patient monitor coupled to the active cable, wherein the active cable includes a visual alarm configured to indicate an alarm condition in response to the physiological data acquired by the plurality of sensors being out of a normal range.

2. The patient monitoring system of claim 1, wherein the active cable converts the physiological data received from the plurality sensors from an analog format to a digital format.

3. The patient monitoring system of claim 1, wherein the active cable converts the physiological data received from the plurality of sensors from an analog format to a digital format, processes the physiological data according to algorithms for a measured parameter to obtain a parameter value and waveform, and sends the parameter value and waveform to the host patient monitor.

4. The patient monitoring system of claim 1, wherein the visual alarm is an LED that is on or off according to the presence of the alarm condition.

5. The patient monitoring system of claim 1, wherein the active cable can be connected to the host patient monitor and disconnected from the host patient monitor in a plug and play fashion.

6. The patient monitoring system of claim 1, wherein active cable is an active cable according to Universal Serial Bus Standards.

7. The patient monitoring system of claim 1, wherein the host patient monitor is configured to selectively enable or disable the visual alarm of the active cable based on operating scenarios.

8. The patient monitoring system of claim 1, wherein the visual alarm is selectively applied only to the alarm condition of high priority.

9. A method for visual alarm indication on parameter active cables, comprising:
   acquiring, at the active cable, physiological sensor data from a plurality of sensors;
   processing the physiological sensor data at the active cable;
   sending the physiological sensor data to a host patient monitor; and
   indicating, on the active cable, an alarm condition in response to the physiological sensor data from the plurality of sensors being out of a normal range.

10. The method of claim 9, wherein processing the physiological sensor data includes converting the physiological sensor data received from the plurality of sensors from an analog format to a digital format.

11. The method of claim 9, wherein processing the physiological sensor data includes converting the physiological sensor data received from the plurality of sensors from an analog format to a digital format, processing the physiological sensor data according to algorithms for a measured parameter to obtain a parameter value and waveform, and sending the physiological sensor data to the host patient monitor includes sending the parameter value and waveform to the host patient monitor.

12. The method of claim 9, wherein the indication of the alarm condition on the active cable is controlled by the host patient monitor.

13. The method of claim 9, wherein the indication of the alarm condition on the active cable is controlled by the physiological sensor data processed at the active cable.

14. The method of claim 9, comprising removing the indication of the alarm condition on the active cable when the alarm condition does not exist.

15. A parameter active cable, comprising:
   a plurality of integrated electronics configured to process physiological data from a plurality of sensors;
   a visible alarm indicator configured to indicate an alarm condition in response to the physiological data from the plurality of sensors being out of a normal range; and
   a communication interface configured to communicate with a host patient monitor.

16. The parameter active cable of claim 15, wherein the visual alarm indicator is an LED.

17. The parameter active cable of claim 15, wherein the communication interface is a communication interface according to a Universal Serial Bus (USB), Universal Asynchronous Receiver/Transmitter (UART), Thunderbolt, Firewire, Display Port, or High-Definition Multimedia Interface (HDMI) Standard.

* * * * *